United States Patent [19]

Norton

[11] Patent Number: 4,671,766

[45] Date of Patent: Jun. 9, 1987

[54] MENISCUS REDUCTION RETENTIVE ORTHOTIC

[76] Inventor: John J. Norton, 1783 Lilac La., St. Paul, Minn. 55118

[21] Appl. No.: 801,611

[22] Filed: Nov. 18, 1985

[51] Int. Cl.[4] ............................................. A61C 3/00
[52] U.S. Cl. ..................................... 433/6; 128/76 R
[58] Field of Search .................. 433/6, 19; 128/76 R, 128/136

[56] References Cited

U.S. PATENT DOCUMENTS

| | | | |
|---|---|---|---|
| 3,513,838 | 5/1970 | Foderick et al. | 128/136 |
| 3,584,620 | 6/1971 | Hale | 128/76 R |
| 4,211,008 | 7/1980 | Lerman | 433/6 |
| 4,457,708 | 7/1984 | Dutour | 433/6 |
| 4,472,139 | 9/1984 | Rosenberg | 433/19 |
| 4,505,672 | 3/1985 | Kurz | 433/6 |
| 4,568,280 | 2/1986 | Ahlin | 433/6 |

Primary Examiner—John J. Wilson
Attorney, Agent, or Firm—Kinney & Lange

[57] ABSTRACT

An intraoral orthotic which consists of two halves, one in the maxillary arch and one in the mandibular arch. Both of which have wings projecting from them which interlock upon closing of the mouth. Each half can be fixed permanently or designed to be removable by the patient. When each half is in the approximate arch and the mouth is closed, the wings on the two pieces engage in a predetermined position to allow the meniscus to be in a proper therapeutic position and to stabilize the surrounding muscles of mastication.

4 Claims, 7 Drawing Figures

MENISCUS REDUCTION RETENTIVE ORTHOTIC

BACKGROUND OF THE INVENTION

This device is an orthotic designed to support the temporomandibular joint (TMJ) in a relatively fixed position thereby allowing the ligaments and muscles to repair.

SUMMARY OF THE INVENTION

This is the only orthotic designed to recapture the meniscus in the TMJ which consists of two independent halves. They function independently during late opening and excursive movements but function as one orthotic in early opening and closing, (whenever the wings are in contact).

Each half can be fixed permanently or be designed to be removable by the patient.

The orthotic is infinitely adjustable according to the biophysiologic needs of the patients temporomandibular joints.

Adjustment is done by altering the shape and size of the wings, i.e. by either adding to or removing acrylic.

During periods of rest or sleep the appliance will stay in function at all times. It will not slip out of function regardless of jaw position during sleep.

DETAILED DESCRIPTION OF THE PREFERRED EMBODIMENTS

Figure 3A:
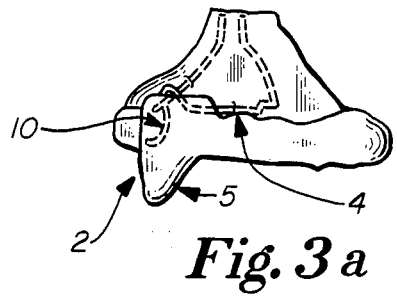
FIG. 3A is a side view of maxillary appliance, (not fitted in position). Note wings projected down.

This is an intraoral orthotic which consists of two parts. One part 2 fits in the maxillary arch and the other part 3 fits in the mandibular arch. Each part is held in position by double or single Adam's clasps, such as that indicated at 4 in FIG. 3A, that attach to the teeth.

The two parts have wings or phalanges on them (to be described in detail later) which interlock in such a manner to maintain the TMJ in the desired theraputic position (see FIG. 4). These phalanges can be adjusted at any time to alter the position of the condyle in the fossa of the TMJ. The phalanges maintain contact throughout the range of motion of the mandible, i.e. open through closing as well as lateral excursions.

Figure 1A:
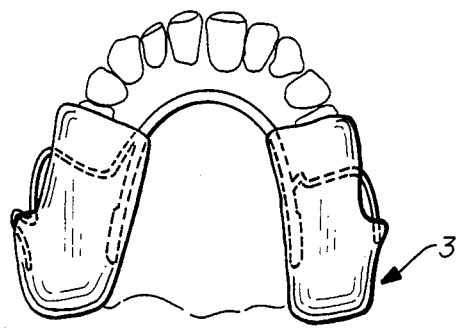
FIG. 1A is a mandibular arch with appliance in place. Note lingual connector bar and wings projecting up and away from appliance base.
Figure 1B:
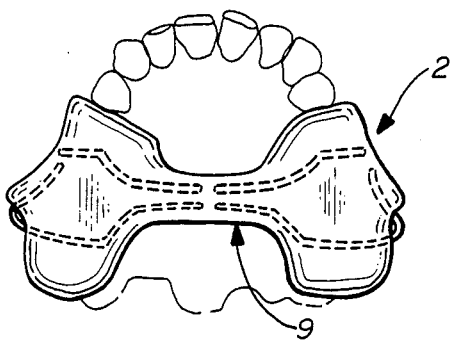
FIG. 1B is a maxillary arch with appliance in place. Note palatal sheath acrylic and wings projecting down from appliance base.
Figure 3B:
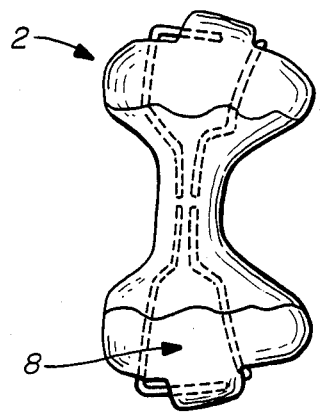
FIG. 3B is a view of maxillary appliance looking up.

The piece fitting in the maxillary arch (see FIGS. 1B, 3A and 3B) is made of acrylic which is formed to fit over the maxillary posterior teeth (bicuspids and molars) for the incisal one-eighth on the buccal surfaces across the occlusal surface thus forming a resting plane 8 for the opposing half in the mandibular arch. It then narrows back toward the molars forming a strap 9 across the last one-third of the hard plate to the opposite side of the maxillary arch. This side is constructed identically to the other side.

There are phalanges (or wings) 5 bilaterally that project down in a triangular shape. These are also made of acrylic and are fabricated as one with the rest of the maxillary half and positioned buccally over the second molar on the maxillary piece. Metal wires or mesh 10 are positioned along the occlusal surfaces and into the phalanges. These wires or mesh 10 are imbedded in the acrylic to act as reinforcement for the phalanges 5.

Figure 2A:
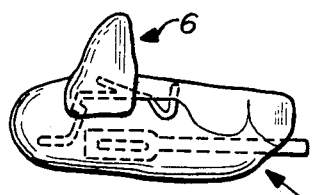
FIG. 2A is a side view of mandibular appliance, (not fitted in position). Note wings projecting up.
Figure 2B:
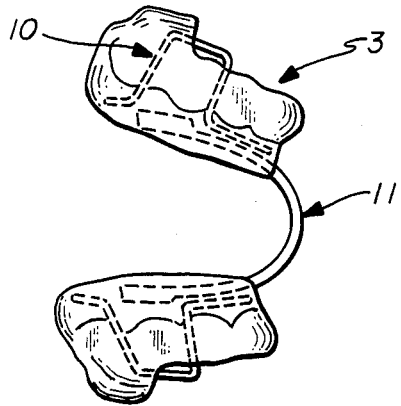
FIG. 2B is a view of the mandibular appliance looking down.

The mandibular half of the appliance (see FIGS. 1A, 2A and 2B) is constructed in a similar method using cold or heat cured acrylic. It is placed to cover one-eighth of the occlusal buccal surface across the occlusal surface and down the lingual surface of the posterior teeth. It also covers part of the lingual gingiva. The right and left halves of the mandibular portion of the orthotic are connected by a lingual metal bar 11 positioned along the gingival lingual surfaces of the lower anterior teeth. An acrylic connector may also be used, however, it is not as strong. Triangular shaped phalanges 6 extending toward the maxillary arch are connected to the lower appliance adjacent buccally to the first molar. These phalanges 6 are constructed in the same manner as the phalanges 5 in the maxillary half of the orthotic.

Figure 4:
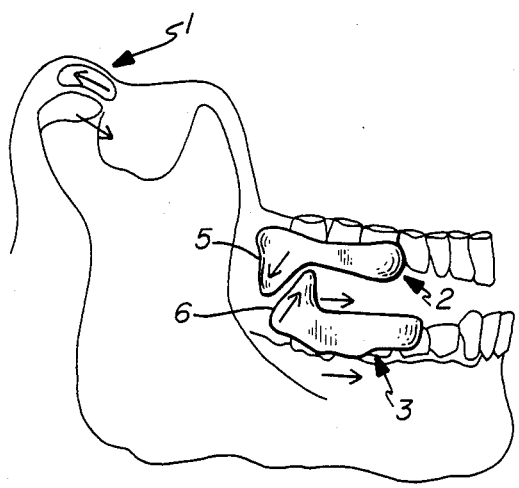
FIG. 4 is a composite functional view of both parts of appliance fitted into respected arches and in function with each other. The arrows on the wings indicated the route of vectors of engagement of the wings. The arrows above the mandibular appliance and below the mandibular appliance on the mandible indicate the resultant vector of movement. The arrows 1 in the joint demonstrate the net effect of the appliance in function. The condyle moves forward and downward, the meniscus moves posterior superiorly.

The thickness of the acrylic on the occlusal surfaces of both halves 2 and 3 varies from 0.5 mm to 3 mm depending on the position needed to treat the temporomandibular joint (see FIG. 4).

The phalanges 5 and 6 are usually between 1.5 mm and 5 mm thick. They range in height between 3 mm and 12 mm depending on the arch relationship of the mandible to the maxilla and the vestibular anatomy.

What is claimed is:

1. A theraputic intraoral orthodic device comprising:
   a first member adapted for securement within the maxillary arch;
   a second member independent of the first member and adapted for securement within the mandibular arch;
   phalange means extending bilaterally from each of said first and second members toward the other of said first and second members, said phalange means having contact surfaces having a predetermining shape so that when the phalange means of one member contacts a phalange means of the other member said surfaces support the temporomandibular joint through at least a portion of its range of motion.

2. The orthodic device of claim 1 wherein the contact between said phalange means supports the temporomandibular joint throughout its range of motion, including lateral excursions.

3. The orthodic device of claim 1 wherein one of said first and second members comprise resting plane means for the other of said first and second members.

4. The orthodic device of claim 1 wherein said phalange means are generally triangular.

* * * * *